(12) United States Patent
Wang

(10) Patent No.: US 10,898,415 B2
(45) Date of Patent: Jan. 26, 2021

(54) FILLERS FOR DENTAL RESTORATIVE MATERIALS

(71) Applicant: Kerr Corporation, Orange, CA (US)

(72) Inventor: Guigui Wang, Orange, CA (US)

(73) Assignee: KERR CORPORATION, Orange, CA (US)

( * ) Notice: Subject to any disclaimer, the term of this patent is extended or adjusted under 35 U.S.C. 154(b) by 101 days.

(21) Appl. No.: 16/238,497

(22) Filed: Jan. 2, 2019

(65) Prior Publication Data

US 2020/0206090 A1 Jul. 2, 2020

(51) Int. Cl.
| | |
|---|---|
| *A61K 6/77* | (2020.01) |
| *A61K 6/887* | (2020.01) |
| *A61C 5/60* | (2017.01) |
| *A61K 6/17* | (2020.01) |
| *A61K 6/75* | (2020.01) |
| *A61K 6/807* | (2020.01) |
| *A61K 6/818* | (2020.01) |

(52) U.S. Cl.
CPC .................. *A61K 6/77* (2020.01); *A61C 5/60* (2017.02); *A61K 6/887* (2020.01); *A61K 6/17* (2020.01); *A61K 6/75* (2020.01); *A61K 6/807* (2020.01); *A61K 6/818* (2020.01)

(58) Field of Classification Search
None
See application file for complete search history.

(56) References Cited

U.S. PATENT DOCUMENTS

| | | | |
|---|---|---|---|
| 4,182,035 A | 1/1980 | Yamauchi et al. | |
| 4,567,030 A | 1/1986 | Yuasa et al. | |
| 4,775,585 A | 10/1988 | Hagiwara et al. | |
| 4,778,834 A | 10/1988 | Murray | |
| 4,781,940 A | 11/1988 | Denton, Jr. | |
| 4,792,632 A | 12/1988 | Ellrich et al. | |
| 4,911,899 A | 3/1990 | Hagiwara et al. | |
| 5,609,675 A | 3/1997 | Noritake et al. | |
| 5,843,348 A | 12/1998 | Giordano | |
| 5,886,064 A | 3/1999 | Rheinberger et al. | |
| 6,159,417 A | 12/2000 | Giordano | |
| 6,818,725 B2 | 11/2004 | Klare et al. | |
| 7,132,459 B1 | 11/2006 | Buchel | |
| 7,495,054 B2 | 2/2009 | Lewandowski et al. | |
| 7,807,227 B2 | 10/2010 | Aechtner et al. | |
| 7,888,400 B2 | 2/2011 | Abuelyaman et al. | |
| 7,943,680 B2 | 5/2011 | Bowman et al. | |
| 7,977,404 B2 | 7/2011 | Wolter et al. | |
| 9,050,252 B2 | 6/2015 | Craig et al. | |
| 9,119,774 B2 | 9/2015 | Gross et al. | |
| 9,193,849 B2 | 11/2015 | Stelzig et al. | |
| 9,340,636 B2 | 5/2016 | Bowman et al. | |
| 2004/0039080 A1 | 2/2004 | Honda et al. | |
| 2004/0176496 A1 | 9/2004 | Han et al. | |
| 2006/0004121 A1 | 1/2006 | Ding et al. | |
| 2006/0160919 A1* | 7/2006 | Brugger .................. A61K 6/54 523/116 |
| 2006/0247329 A1 | 11/2006 | Moszner et al. | |
| 2011/0082232 A1 | 4/2011 | Gross et al. | |
| 2012/0225201 A1 | 9/2012 | Glueck et al. | |
| 2014/0051782 A1 | 2/2014 | Cheetham et al. | |
| 2015/0250687 A1 | 9/2015 | Bowman et al. | |
| 2015/0267002 A1 | 9/2015 | Bowman et al. | |
| 2016/0324729 A1 | 11/2016 | Hokii et al. | |

FOREIGN PATENT DOCUMENTS

| | | | | |
|---|---|---|---|---|
| CA | 1290888 C | * | 10/1991 | ................ C08F 2/44 |
| CA | 1290888 C | | 10/1991 | |
| CN | 102895126 B | | 7/2014 | |
| CN | 105193634 A | | 12/2015 | |
| EP | 0262488 B1 | | 6/1990 | |
| EP | 0716103 B1 | | 5/1999 | |
| EP | 2799496 A1 | | 11/2014 | |
| EP | 3135271 A1 | | 3/2017 | |
| JP | 2013095690 A | | 5/2013 | |
| WO | 9221632 A2 | | 12/1992 | |
| WO | WO-9221632 A2 | * | 12/1992 | ............ C07F 7/1804 |
| WO | WO 2013/087223 A1 | | 6/2013 | |
| WO | WO-2013087223 A1 | * | 6/2013 | ............ C09D 143/04 |

OTHER PUBLICATIONS

International Search Report and Written Opinion for Application No. PCT/US2019/012110 dated Oct. 9, 2019 (15 pages).

* cited by examiner

*Primary Examiner* — Peter A Salamon
(74) *Attorney, Agent, or Firm* — Michael Best & Friedrich LLP

(57) ABSTRACT

Described herein are directed to dental filler particles and methods of making the same. The dental filler particles include a polymer coating with a plurality of ethylenically unsaturated groups on the surface of the coating. Also described herein are dental restorative materials comprising the particles.

24 Claims, No Drawings

FILLERS FOR DENTAL RESTORATIVE MATERIALS

TECHNICAL FIELD

Embodiments are directed to dental filler particles. The dental filler particles include a polymer coating with a plurality of ethylenically unsaturated groups on the surface of the coating. Other embodiments are directed to methods of making the particles, and dental restorative materials comprising the particles.

BACKGROUND

Posterior and anterior tooth restorations are typically achieved by excavating decayed tooth structure and filling the resulting cavity with a paste-like filling material, which is then hardened by chemical or photochemical curing processes. Resin based dental restorative materials are becoming the materials of choice by dentists and patients due to desirable aesthetic properties. Tooth-colored resin based composite materials are usually composed of dispersions of inorganic filler particles in a polymerizable organic resin matrix.

Stress-bearing restorations, such as those involving the occlusal surface of posterior teeth, require the use of mechanically strong, highly filled restorative materials to withstand the forces resulting from mastication. Such restorative materials are typically highly viscous, which can make accurate placement of the restorative difficult and technique-sensitive. Inadvertently, the cavity may be insufficiently filled and adaptation of the restorative material to the cavity walls may be incomplete, resulting in gaps between the restoration and the tooth structure, which can lead to increased sensitivity, intrusion of fluids and bacteria, continued tooth decay, and premature failure of the restoration. Less highly-filled, flowable restorative materials, on the other hand, facilitate proper adaptation but lack the required strength for stress bearing restorations. Moreover, because these less highly filled materials tend to flow under their own weight, they often cannot be shaped to conform to the original tooth anatomy.

Dental composite materials with a balance of aesthetic properties and mechanical strength are highly desirable.

SUMMARY

In one aspect, disclosed is a dental filler particle. The dental filler particle comprises an inorganic particle and a polymer coating on a surface of the inorganic particle. The polymer coating comprises structural units derived from: (a) a first monomer having a silane group and an ethylenically unsaturated group; (b) a second monomer having at least one ethylenically unsaturated group and at least one functional group selected from the group consisting of a hydroxyl group, an amino group, a carboxyl group and combinations thereof; and (c) a third monomer having at least one ethylenically unsaturated group and at least one isocyanate group, wherein the dental filler particle comprises a plurality of ethylenically unsaturated groups on a surface of the polymer coating.

In another aspect, disclosed is a method of making dental filler particles, the method comprising:

(a) treating inorganic particles with a first monomer having a silane group and an ethylenically unsaturated group, to provide silane-treated particles;

(b) adding a second monomer and a polymerization initiator to the silane-treated particles to form a mixture, wherein the second monomer has at least one ethylenically unsaturated group and at least one functional group selected from the group consisting of a hydroxyl group, an amino group, and a carboxyl group;

(c) polymerizing the mixture to provide polymer-coated particles; and (d) reacting the polymer-coated particles with a third monomer having an ethylenically unsaturated group and an isocyanate group, to provide the dental filler particles.

In another aspect, disclosed are dental restorative compositions comprising a polymerizable resin and a plurality of the dental filler particles.

In another aspect, disclosed are methods of performing dental restoration that include applying the dental restorative composition to a tooth structure, and hardening the dental composition.

In another aspect, disclosed are dental restorative kits that include the dental restorative composition, and instructions for using the dental restorative composition.

DETAILED DESCRIPTION

Among other things, disclosed herein are dental filler particles. The particles are coated with a polymer coating such that the surface of the coating comprises a plurality of ethylenically unsaturated groups. When the particles are incorporated into a dental composite composition that includes a polymerizable resin, the unsaturated groups can react with the resin during curing. Use of such particles can provide a composite with improved mechanical strength and translucency.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

2. DENTAL FILLER PARTICLES

Disclosed herein are dental filler particles that comprise an inorganic particle and a polymer coating on a surface of the inorganic particle. The particles comprise a plurality of ethylenically unsaturated groups on a surface of the polymer coating, which can react with a polymerizable resin during curing of a dental composite, providing a composite with good aesthetic properties along with high mechanical strength.

a. Inorganic Particles

The dental filler particle comprises an inorganic particle. The inorganic particle is selected from the group consisting of borosilicate glass, barium magnesium aluminosilicate glass, barium aluminosilicate glass, glass powder, silica, zirconium silicate, titanium silicate, barium oxide, quartz, alumina, glass fiber, clay, calcium phosphate, hydroxyapatite, an inorganic oxide, an aggregate of two or more inorganic oxides, and any combination thereof. In embodiments, the inorganic particle comprises an aggregate of two or more oxides, wherein the oxides are selected from the group consisting of silica, zirconia, barium oxide, titania, alumina, and zinc oxide.

In one embodiment, the mean particle size of the inorganic particles is about 0.001 micron to about 100 microns. In one embodiment, the mean particle size of the inorganic particles is less than 50 microns. In another embodiment, the mean particle size of the inorganic particles is less than 10 microns. In another embodiment, the mean particle size of the inorganic particles is less than 5 microns. In another embodiment, the mean particle size of the inorganic particles is less than 2 microns.

The inorganic particles can be prepared by a chemical sol gel process, or in an embodiment, the inorganic particles filler may be ground to the size range by a commination step.

Examples of inorganic particles include, but are not limited to those disclosed in U.S. Pat. Nos. 4,567,030 and 5,609,675, the disclosure of each expressly incorporated by reference herein in its entirety.

b. Polymer Coating

The inorganic particles include a polymer coating. The coating comprises structural units derived from:

(a) a first monomer having a silane group and an ethylenically unsaturated group;

(b) a second monomer having at least one ethylenically unsaturated group and at least one functional group selected from the group consisting of a hydroxyl group, an amino group, a carboxyl group and combinations thereof; and (c) a third monomer having at least one ethylenically unsaturated group and at least one isocyanate group.

The first monomer has a silane group and an ethylenically unsaturated group. The silane group can react with the surface of the inorganic particles, providing silane-treated particles with the ethylenically unsaturated group on the surface. The ethylenically unsaturated group can be selected from the group consisting of acrylate, methacrylate, acrylamide, methacrylamide, and vinyl groups, or any combination thereof. In embodiments, the first monomer is selected from the group consisting of 3-methacryloxypropyltrimethoxysilane, 3-methacryloxypropyltriethoxysilane, and acryloxypropyltrimethoxysilane.

The second monomer has at least one ethylenically unsaturated group and at least one functional group selected from the group consisting of a hydroxyl group, an amino group, a carboxyl group and combinations thereof. The ethylenically unsaturated group can be selected from the group consisting of acrylate, methacrylate, acrylamide, methacrylamide, and vinyl groups, or any combination thereof. The ethylenically unsaturated group(s) of the second monomer react with the ethylenically unsaturated groups derived from the silane group of the first monomer, in a polymerization reaction to provide an inorganic particle with a polymer coating on the surface. The polymer coating includes a plurality of functional groups on the surface, which are available for further reaction with the third monomer.

In embodiments, the second monomer is selected from the group consisting of 2,2-bis[4-(2-hydroxy-3-methacryloylpropoxy)-phenyl]propane (BisGMA), 2-hydroxyethyl (meth)acrylate, hydroxypropyl (meth)acrylate, hydroxybutyl (meth)acrylate, hydroxypolyethoxyethyl (meth)acrylate, hydroxylpolypropoxyethyl (meth)acrylate, hydroxypolyethoxy allyl ether, glycerol di(meth)acrylate, and glyceryl mono(meth)acrylate, or a mixture of any thereof. In an embodiment, the second monomer is BisGMA. In an embodiment, the second monomer is 2-hydroxyethyl methacrylate. In an embodiment, the second monomer comprises a mixture of two monomers, each monomer independently having at least one ethylenically unsaturated group and at least one functional group selected from the group consisting of a hydroxyl group, an amino group, a carboxyl group and combinations thereof. In an embodiment, the second monomer comprises a mixture of BisGMA and 2-hydroxyethyl methacrylate.

The third monomer has at least one ethylenically unsaturated group and at least one isocyanate group. The isocyanate group can react with the functional group derived from the second monomer, to provide the product inorganic particle with a plurality of double bonds on the surface. In embodiments, the third monomer is 2-isocyanatoethyl (meth)acrylate (e.g., 2-isocyanatoethyl methacrylate).

In embodiments, the polymer coating has formula (I):

—X—Y—Z    (I), wherein

X is a structural unit derived from the first monomer and is bonded to the inorganic particle via the silane group;

Y is a structural unit derived from the second monomer; and

Z is a structural unit derived from the third monomer.

3. METHODS OF MAKING DENTAL FILLER PARTICLES

Also disclosed herein are methods of making dental filler particles, the method comprising:

(a) treating inorganic particles with a first monomer having a silane group and an ethylenically unsaturated group, to provide silane-treated particles;

(b) adding a second monomer to the silane-treated particles to form a mixture, wherein the second monomer has at least one ethylenically unsaturated group and at least one functional group selected from the group consisting of a hydroxyl group, an amino group, and a carboxyl group;

(c) polymerizing the mixture to provide polymer-coated particles; and (d) reacting the polymer-coated particles with a third monomer having an ethylenically unsaturated group and an isocyanate group, to provide the dental filler particles.

In these embodiments, the inorganic particles, the first monomer, the second monomer, and the third monomer are the same as those described above regarding the dental filler particles.

In embodiments, a polymerization initiator is added to the silane-treated particles with the second monomer in step (b). The polymerization initiator can be selected from the group consisting of a heat initiator and a photo-initiator, or a combination thereof. When a photoinitiator is used, the photoinitiator can be any compound that would generate free radicals upon exposure to a light source and cause the polymerization. The light source can be any light that emits light in the visible or ultraviolet range. Examples of photoinitiators include, but are not limited to, benzoin, benzoin ethers and esters, 2,2-diethoxy acetophenone, diketone compounds such as camphorquinone and 1-phenyl-1,2-propanedione, monoacylphosphine oxide, bisacylphosphine oxide as disclosed in U.S. Pat. No. 4,792,632, which is expressly incorporated by reference herein in its entirety, diaryliodonium salt, triarylsulfonium salt, and a mixture of photoinitiators.

Additionally, a co-initiator can be used together with a photoinitiator to enhance curing efficiency. Co-initiators include tertiary amine and sulfinate compounds. Examples of co-initiators include, but are not limited to, ethyl-4-(N,N-dimethylamino) benzoate (EDMAB), 2-ethylhexyl-4-(N,N-dimethylamino) benzoate (ODMAB), 4-dimethylaminobenzophenone (DMABP), p-dimethylamino benzoic acid (DMABA), p-(dimethylamino) benzonitrile (DMABCN), p-(dimethylamino) benzaldehyde, 4'-morpholino-acetophenone, 4'-morpholino-benzophenone, p-(dimethylamino) acetophenone, 4,4'-bis(dimethylamino)benzophenone, 4,4'-bis(diethylamino) benzophenone and dimethylaniline. Among these tertiary amines, EDMAB, ODMAB, DMABP, DMABA and DMABCN are exemplary. Other reducing agents for camphorquinone include but are not limited to chemical compounds with urethane and benzhydyl groups.

Phosphine oxides, including mono-acyl and multi-acyl phosphine oxide, can also be used as photoinitiators. Phosphine oxides can initiate free radical polymerizations by themselves under ultraviolet and/or visible irradiations generated by a typical dental curing device. Examples of phosphine oxides include, but are not limited to, bis(2,4,6-trimethylbenzoyl)-phenyl phosphine oxide (Irgacure 819, Ciba Specialty Chemicals, Basel, Switzerland), bis(2,6-dimethoxybenzoyl)-(2,4,4-trimethylpentyl) phosphine oxide (CGI 403, Ciba Specialty Chemicals) and ethyl 2,4,6-trimethylbenzoyl-phenyl phosphine oxide (LUCIRIN LR8893X, BASF Corp., Charlotte, N.C.). Combinations of two or more phosphine oxides are also advantageous. Examples of combinations of phosphine oxides include, but are not limited to, a 50:50 by weight mixture of 2,4,6-trimethylbenzoyl-diphenyl phosphine oxide and 2-hydroxy-2-methyl-1-phenylpropane-1-one (DAROCUR 4265, Ciba Specialty Chemicals).

In the disclosed method, step (a) produces silane-treated particles with an ethylenically unsaturated group on the surface. Reaction of that ethylenically unsaturated group with the second monomer in step (b), where the second monomer also includes an ethylenically unsaturated group, produces an inorganic particle with a polymer coating that includes a functional group on the surface, selected from a hydroxyl group, an amino group, and a carboxyl group (or a combination of any thereof). That functional group can then react with the isocyanate group of the third monomer to provide particles having a plurality of ethylenically unsaturated groups on the surface. The dental filler particles produced by the method may have an average diameter of about 0.001 micron to about 100 microns.

4. DENTAL RESTORATIVE COMPOSITIONS

Also disclosed herein are dental restorative compositions comprising a polymerizable resin and a plurality of dental filler particles, where the dental filler particles comprise at least one filler described herein that has a plurality of ethylenically unsaturated groups on the surface.

a. Polymerizable Resin

The polymerizable resin includes one or more polymerizable monomers, each having at least one ethylenically unsaturated group. Examples of ethylenically unsaturated groups include, but are not limited to, acrylate, methacrylate, acrylamide, methacrylamide, and vinyl group. Examples of polymerizable monomers include, but are not limited to, the following: hydroxyethyl(meth)acrylate {(meth) acrylate=acrylate or methacrylate}, hydroxypropyl (meth) acrylate, hydroxybutyl (meth)acrylate, glycerol di(meth) acrylate, glycerol mono(meth)acrylate, methyl(meth) acrylate, ethyl(meth)acrylate, propyl(meth)acrylate, butyl (meth)acrylate, hexyl(meth)acrylate, octyl(meth)acrylate, lauryl(meth)acrylate, decyl(meth)acrylate, tridecyl(meth) acrylate, 2-ethoxyethyl(meth)acrylate, 2'-ethoxy-2-ethoxyethyl(meth)acrylate, ethyleneglycol di(meth)acrylate, diethyleneglycol di(meth)acrylate, triethyleneglycol di(meth) acrylate (TEGDMA), tetraethyleneglycol di(meth)acrylate, polyethyleneglycol mono-(meth)acrylate, polyethyleneglycol di(meth)acrylate, polypropyleneglycol mono-(meth) acrylate, polypropyleneglycol di(meth)acrylate, polytetramethyleneglycol mono-(meth)acrylate, polytetramethyleneglycol di(meth)acrylate, hexanediol di(meth)acrylate, trimethyloylpropane tri(meth)acrylate, ethoxylated trimethyloylpropane tri(meth)acrylate, UDMA (reaction product of 2-hydroxyethyl methacrylate with 2,4,4-trimethylhexane diisocyanate), 2,2-bis[4-(2-hydroxy-3-methacryloylpropoxy)-phenyl]-propane (Bis-GMA), ethoxylated bisphenol A dimethacrylate ("EBPADMA-n", n=total number of moles of ethylene oxide in the molecule, with 2-20 units being preferred), tetrahydrofurfuryl (meth) acrylate, N,N'-methylenebis(acrylamide), N,N'-ethylenebis (acrylamide), N,N'-butylenebis(acrylamide), or a mixture of one or more of any thereof. In one embodiment, the polymerizable resin comprises at least one polymerizable monomer having at least one hydroxyl group. Examples of hydroxyl-containing polymerizable monomers include, but are not limited to, hydroxyethyl (meth)acrylate, hydroxypropyl (meth)acrylate, hydroxybutyl (meth)acrylate, glycerol di(meth)acrylate, glycerol mono(meth)acrylate, and Bis-GMA.

In one embodiment, the polymerizable resin comprises one or more polymerizable monomers having at least two ethylenically unsaturated groups.

In one embodiment, the polymerizable resin further comprises one or more acidic polymerizable monomers having at least one ethylenically unsaturated group and at least one acidic moiety. The acidic moiety can be any acidic functional group. Examples of acidic moieties include, but are not limited to, carboxylic acid, carboxylic acid anhydride, phosphonic acid, phosphonic acid ester, phosphoric acid, phosphoric acid ester, sulfonic acid, sulfinic acid, and combinations thereof. In one embodiment, the acidic polymerizable monomer contains at least one acidic moiety selected from the group consisting of phosphonic acid, phosphonic acid ester, phosphoric acid, or phosphoric acid ester. Examples of acidic monomers include, but are not limited to, phenyl methacryloxyethyl phosphate, glyceryldimethacrylate phosphate, dipentaerithritol pentaacrylate phosphate, methacryloyloxybutyl phosphate, methacryloyloxyhexyl phosphate, methacryloyloxydecyl phosphate, hydroxyethylmethacrylate phosphate, and bis(hydroxyethylmethacrylate) phosphate, and any combination thereof. In another embodiment, the acidic monomer contains at least one acidic moiety selected from the group consisting of carboxylic acid and carboxylic anhydride. Examples include, but are not limited to, maleic acid, itaconic acid, methacrylic acid, acrylic acid, polymerizable homopolymer or copolymer of an α,β-unsaturated carboxylic acid such as (meth)acrylated poly(acrylic acid), (meth)acrylated poly(acrylic acid) copolymer such as (meth)acrylated poly(acrylic acid-maleic acid) copolymer or (meth)acrylated poly(acrylic acid-maleic acid-itaconic acid) copolymer, maleic anhydride, 4-methacryloxyethyltrimellitic anhydride, 4-methacryloxyethyltrimellitic acid, any addition product of mono- or di-anhydride compound with an hydroxyalkylmethacrylate compound such as the addition product of pyromellitic acid anhydride and 2-hydroxyethyl methacrylate, the addition product of pyromellitic acid anhydride and glycerol dimethacrylate, the addition product of 3,3',4,4'-benzophenonetetracarboxylic dianhydride and hydroxyethyl methacrylate, the addition product of phthalic anhydride and hydroxyethyl methacrylate, the addition product of maleic anhydride and glycerol dimethacrylate, and any combination thereof.

The polymerizable resin may be included in the composition in an amount of about 10% to about 99% by weight, e.g., about 10% to about 80% by weight, or about 20% to about 70% by weight.

b. Dental Filler Particles

The dental restorative compositions also include dental filler particles described herein, which have a polymer coating having plurality of ethylenically unsaturated groups on the surface. Such particles have been described above.

The dental filler particles may be included in the composition in an amount of about 1% to about 90% by weight, e.g., about 20% to about 90% by weight, or about 30% to about 80% by weight.

c. Other Components

In some embodiments, the dental restorative compositions can further comprise one or more additional components selected from the group consisting of a polymerization initiator, a stabilizer, a UV absorber, a fluorescent agent, a fluoride releasing agent, a radiopaque agent, and an antimicrobial agent.

The polymerization initiator that may be included in the dental restorative composition may be the same as or different from the polymerization initiator that may be used to prepare the dental filler particles.

The stabilizer may be a polymerization inhibitor or retarder, which may improve the shelf stability of the restorative material. Most commonly used stabilizers include 2,6-di-(tert-butyl)-4-methylphenol ("BHT") and 4-methoxyphenol ("MEHQ"). The concentration for the stabilizer may be between 0.0001 and 5% by weight, for example, greater than 0.01% or greater than 0.1%, and by further example, less than 4% or less than 3% by weight.

The UV absorber is used to improve the color stability of the dental material upon exposure to UV light. An example of UV absorber is 2-hydroxy-4-methoxybenzophenone ("UV-9").

A fluorescent agent may impart special optical properties to improve aesthetics, or may serve as an aid for identifying the composite material in case there is a need to remove it.

A fluoride releasing agent is any fluoride-containing substance that can release fluoride into saliva or water. Examples of fluoride compounds include, but are not limited to, sodium fluoride, potassium fluoride, calcium fluoride, strontium fluoride, magnesium fluoride, sodium hexafluorosilicate, zinc hexafluorosilicate, strontium hexafluorosilicate, ytterbium fluoride, a salt formed by an amine and HF, a complex formed by an amine and $BF_3$, and any combination thereof.

A radiopaque agent may provide increased X-ray contrast ability. Examples of radiopaque inorganic fillers include metals, salts, oxides, fluorides, silicate glass, aluminosilicate glass, aluminoborosilicate glass, and fluoroaluminosilicate glass containing elements of high atomic number such as Sr, Y, Zr, Ba, La, Hf, Zn, Bi, W, rare earth metals, and combinations of these.

Examples of antimicrobial additives include, but are not limited to, benzalkonium chloride, iodoform, eugenol, zinc oxide, triclosan, alkyl 4-hydroxybenzoate, silicate glass powder containing silver and/or zinc, and zeolite powder containing silver and/or zinc ion(s). Useful antibacterial zeolites and their preparation are disclosed in U.S. Pat. Nos. 4,911,899 and 4,775,585, each of which is incorporated by reference herein in its entirety.

d. Properties of Dental Restorative Compositions

The dental restorative compositions may include properties that balance mechanical strength and aesthetic needs, including flexural strength, Vickers hardness and opacity.

The dental compositions may have high flexural strength. The flexural strength may be about 60 MPa to about 300 MPa.

The dental compositions may have high modulus strength. The modulus strength may be about 6 GPa to about 18 GPa.

The dental compositions may have good Vickers hardness. The Vickers hardness may be about 400 to about 1100 MPa.

The dental compositions may have opacity which allows the restorative to a lifelike appearance. The opacity may be less than about 80%.

5. METHODS OF USE AND KITS

Also disclosed herein are methods of using the dental composition. In particular, disclosed are methods of performing dental restoration using the dental composition. The methods may include applying the dental composition to a tooth structure. The dental composition may then be hardened, e.g., by polymerization of the monomers in the polymerizable resin. Polymerization of the monomers may be initiated, for example, through light activation with a dental curing light capable of generating ultraviolet and/or visible light.

The disclosed dental restorative compositions may be used in kits, e.g., kits for use in restorative dental applications. The kit may include the disclosed dental restorative compositions and instructions for using the dental composition.

In some embodiments, the dental restorative composition is separated into two or more compositions for enhanced performance or shelf-life stability. Accordingly, for these embodiments, the instructions also describe how to combine the separate compositions just before application to provide the dental composition. In some embodiments, the kit may include another dental composition selected from the group consisting of an etchant, a primer, an adhesive, a cement, a composite, or any combination thereof.

6. EXAMPLES

Example 1. Synthesis of Exemplary Particles

Particles were prepared using zirconia-silica inorganic particles, 3-methacryloxypropyltrimethoxysilane as the first monomer, BisGMA and/or HEMA as the second monomer, and 2-isocyanatoethyl methacrylate as the third monomer.

The particles may be produced by any method known in the art. For example, the inorganic particles were mixed with the first monomer in an appropriate solvent. Following solvent evaporation and drying, the particles were mixed with the second monomer in an appropriate second solvent. Following evaporation of the second solvent, the resulting polymer coated particles were mixed with the third monomer and an appropriate catalyst to facilitate the reaction between the functional group of the second monomer and the isocyanate group of the third monomer. The solid particles were filtered from the reaction mixture and dried in vacuum oven.

Example 2. Particle Properties

The particles were combined with a polymerizable resin and certain particle properties are described in Table 1.

TABLE 1

| Filler type | Control - no double bonds on surface | Second monomer = BisGMA | Second monomer = BisGMA/HEMA 50/50 | Second monomer = HEMA |
|---|---|---|---|---|
| % Resin | 27.5 | 27.5 | 27.5 | 27.5 |
| % filler | 72.5 | 72.5 | 72.5 | 72.5 |
| L | 83.14 | 81.78 | 81.76 | 77.14 |
| a | −4.47 | −5.91 | −5.78 | 3.62 |
| b | 12.64 | 18.91 | 19.86 | 38.01 |
| % Opacity | 53.63 | 51.16 | 50.46 | 68.93 |
| Flexural strength (MPa) | 126 | 142 | 141 | 114 |
| Modulus strength (MPa) | 8644 | 10886 | 9864 | 8725 |
| Vickers hardness (MPa) | 586 | 639 | 635 | 523 |

Example 3. Dental Restorative Properties

The particles were combined with a polymerizable resin. The inorganic filler was infused into the composition using two different methods as noted in Table 2. Method 2 allows for higher maximum filler loading. Method 2 shows increased flexural strength, modulus strength, Vickers hardness, while retaining similar initial gloss but better gloss retention. Method 2 also allowed for decreased opacity.

TABLE 2

|  | Infusion Method 1 | Infusion Method 2 |
|---|---|---|
| % Resin | 26.5 | 19.4 |
| % filler, maxi loading | 73.4 | 80.6 |
| L | 88.48 | 80.85 |
| a | −3.8 | −3.83 |
| b | 9.32 | 14.17 |
| % Opacity | 62.39 | 47.12 |
| Flexural strength (MPa) | 122 | 150 |
| Modulus strength (MPa) | 8283 | 11403 |
| Vickers hardness (MPa) | 527 | 720 |
| Initial gloss | 79.5 | 79.6 |
| Gloss retention after 4 hrs | 50.3 | 57.6 |

Different infusion solutions (monomer mixture) were screened using Infusion Method 2. The infused fillers were used to make composite paste with 72.5% infused fillers and 27.5% resin and the final properties of cured paste were compared (Table 3). Infusion with 100% BisGMA produced the best final paste properties among the three combinations. However all monomer mixtures produced a final paste with opacities less than 70%, flexural strength greater than 100 Mpa and Vickers hardness greater than 500.

TABLE 3

| Filler type | Infusion Method 2 BisGMA | Infusion Method 2 BisGMA/HEMA 50/50 | Infusion Method 2 HEMA |
|---|---|---|---|
| % Resin | 27.5 | 27.5 | 27.5 |
| % filler | 72.5 | 72.5 | 72.5 |
| L | 81.78 | 81.76 | 77.14 |
| a | −5.91 | −5.78 | 3.62 |
| b | 18.91 | 19.86 | 38.01 |
| % Opacity | 51.16 | 50.46 | 68.93 |
| Flexural strength (MPa) | 142 | 141 | 114 |
| Modulus strength (MPa) | 10886 | 9864 | 8725 |
| Vickers hardness (MPa) | 639 | 635 | 523 |

Different types of inorganic fillers were screened using both Infusion Methods (Table 4). Infusion Method 2 showed increased flexural strength and Vickers hardness with both types of fillers tested.

TABLE 4

|  | Infusion Method 1 | Infusion Method 2 | Infusion Method 1 | Infusion Method 2 |
|---|---|---|---|---|
| % Resin | 27 | 27 | 27 | 27 |
| % filler | 73 | 73 | 73 | 73 |
| Filer type | A1 | A1 | B | B |
| L | 83.03 | 82.21 | 84.95 | 81.59 |
| a | −4.32 | −6.98 | −4.39 | −6.15 |
| b | 12.4 | 20.04 | 10.91 | 19.55 |
| % Opacity | 46.72 | 44.02 | 52.38 | 48.5 |
| Flexural strength (MPa) | 105.8 (16) | 173.3 (28) | 105 (17) | 159 (19) |

TABLE 4-continued

|  | Infusion Method 1 | Infusion Method 2 | Infusion Method 1 | Infusion Method 2 |
| --- | --- | --- | --- | --- |
| Modulus strength (MPa) | 8838 (1334) | 11345 (520) | 8902 (740) | 9585 (885) |
| Vickers hardness (MPa) | 520 | 644 | 512 | 598 |

With another paste formulation different from the above, Infusion Method 2 was still able to result in increased flexural strength and decreased opacity (Table 5). In addition to higher FS and lower opacity, Infusion Method 2 also showed lower paste viscosity at the same total filler loading, which makes higher filler loading formulation possible to further strengthen the mechanical properties.

TABLE 5

|  | Infusion Method 1 | Infusion Method 2 |
| --- | --- | --- |
| % Resin | 27 | 27 |
| % filler-MO | 70 | 70 |
| Filer type | A2 | A2 |
| % Filler-TS530 | 2 | 2 |
| Final percent loading | 72 | 72 |
| Flexural strength (MPa) | 126.1 | 143 |
| Modulus strength. (MPa) | 10366 | 9444 |
| Complex viscosity (eta*) | 12.3 | 7.99 |
| Opacity after cure | 50.12 | 39.69 |

Various features and advantages of some embodiments are set forth in the following claims.

What is claimed is:

1. A dental filler particle comprising:
   an inorganic particle; and
   a polymer coating on a surface of the inorganic particle, comprising structural units derived from:
   (a) a first monomer having a silane group and an ethylenically unsaturated group;
   (b) a second monomer having at least one ethylenically unsaturated group and at least one functional group selected from the group consisting of a hydroxyl group, an amino group, a carboxyl group and combinations thereof; and
   (c) a third monomer having at least one ethylenically unsaturated group and at least one isocyanate group,
   wherein the dental filler particle comprises a plurality of ethylenically unsaturated groups on a surface of the polymer coating.

2. The dental filler particle of claim 1, wherein each ethylenically unsaturated group is independently selected from the group consisting of acrylate, methacrylate, acrylamide, methacrylamide, and vinyl groups.

3. The dental filler particle of claim 1, wherein the second monomer is incorporated into the polymer coating using a polymerization initiator selected from the group consisting of a heat initiator and a photo-initiator, or a combination thereof.

4. The dental filler particle of any of claim 1, wherein the polymer coating has formula (I):

wherein
X is a structural unit derived from the first monomer and is bonded to the inorganic particle via the silane group;
Y is a structural unit derived from the second monomer; and
Z is a structural unit derived from the third monomer.

5. The dental filler particle of claim 1, wherein the first monomer is selected from the group consisting of 3-methacryloxypropyltrimethoxysilane, 3-methacryloxypropyltriethoxysilane, and acryloxypropyltrimethoxysilane.

6. The dental filler particle of claim 1, wherein the second monomer is selected from the group consisting of 2,2-bis[4-(2-hydroxy-3-methacryloylpropoxy)-phenyl]propane (BisGMA), 2-hydroxyethyl (meth)acrylate, hydroxypropyl (meth)acrylate, hydroxybutyl (meth)acrylate, hydroxypolyethoxyethyl (meth)acrylate, hydroxylpolypropoxyethyl (meth)acrylate, hydroxypolyethoxy allyl ether, glycerol di(meth)acrylate, and glyceryl mono(meth)acrylate, or a mixture of any thereof.

7. The dental filler particle of claim 6, wherein the second monomer comprises a mixture of BisGMA and 2-hydroxyethyl (meth)acrylate.

8. The dental filler particle of claim 1, wherein the third monomer is 2-isocyanatoethyl methacrylate.

9. The dental filler particle of claim 1, having an average particle diameter of from about 0.001 micron to about 100 microns.

10. The dental filler particle of claim 1, wherein the inorganic particle is selected from the group consisting of borosilicate, barium aluminosilicate glass, glass powder, silica, silica powder, titanium silicate, zirconium silicate, quartz, glass fiber, clay, calcium phosphate, hydroxyapatite, an oxide, an aggregate of two or more oxides, and any combination thereof.

11. The dental filler particle of claim 10, wherein the oxide or oxides are selected from the group consisting of silica, zirconia, barium oxide, titania, alumina, zinc oxide, and combinations thereof.

12. A dental restorative composition comprising:
   a polymerizable resin; and
   a plurality of dental filler particles comprising at least one filler of claim 1.

13. The dental restorative composition of claim 12, wherein the composition comprises the polymerizable resin in an amount of about 10% to about 99% by weight.

14. The dental restorative composition of claim 12, wherein the composition comprises the dental filler particles in an amount of about 1% to about 90% by weight.

15. The dental restorative composition of claim 12, wherein the polymerizable resin comprises at least one monomer having at least one ethylenically unsaturated group.

16. The dental restorative composition of claim 12, wherein the polymerizable resin comprises at least one acidic monomer having at least one ethylenically unsaturated group and at least one acidic moiety selected from the group consisting of carboxylic acid, carboxylic acid anhydride, phosphonic acid, phosphonic acid ester, phosphoric acid, phosphoric acid ester, sulfonic acid, sulfinic acid, and combinations thereof.

17. The dental restorative composition of claim 12, further comprising one or more components selected from the group consisting of a polymerization initiator, a stabilizer, a UV absorber, a fluorescent agent, a fluoride releasing agent, a radiopaque agent, and an antimicrobial agent.

18. A dental restorative kit comprising:
   the dental restorative composition of claim 12; and
   instructions for using the dental restorative composition.

19. A method of making dental filler particles, the method comprising:

(a) treating inorganic particles with a first monomer having a silane group and an ethylenically unsaturated group, to provide silane-treated particles;
(b) adding a second monomer to the silane-treated particles to form a mixture, wherein the second monomer has at least one ethylenically unsaturated group and at least one functional group selected from the group consisting of a hydroxyl group, an amino group, and a carboxyl group;
(c) polymerizing the mixture to provide polymer-coated particles; and
(d) reacting the polymer-coated particles with a third monomer having an ethylenically unsaturated group and an isocyanate group,
to provide the dental filler particles.

20. The method of claim 19, wherein during step (b), a polymerization initiator is added to the silane-treated particles with the second monomer, wherein the polymerization initiator is selected from the group consisting of a heat initiator and a photo-initiator, or a combination thereof.

21. The method of claim 19, wherein after step (c), the polymer-coated particles comprise a plurality of hydroxyl, amino and/or carboxyl groups on a surface of the polymer-coated particles.

22. The method of claim 19, wherein after step (d), the dental filler particles comprise a plurality of ethylenically unsaturated groups on a surface of the dental filler particles.

23. The method of claim 19, wherein the dental filler particles have an average diameter of about 0.001 micron to about 100 microns.

24. A method of performing dental restoration, the method comprising:
(i) applying the dental restorative composition of claim 12 to a tooth structure; and
(ii) hardening the dental restorative composition.

* * * * *